US005636644A

United States Patent [19]
Hart et al.

[11] Patent Number: 5,636,644
[45] Date of Patent: Jun. 10, 1997

[54] METHOD AND APPARATUS FOR ENDOCONDUIT TARGETING

[75] Inventors: Charles C. Hart, Huntington Beach; Donald L. Gadberry, San Juan Capistrano; Eduardo Chi Sing, Laguna Niguel, all of Calif.

[73] Assignee: Applied Medical Resources Corporation, Laguna Hills, Calif.

[21] Appl. No.: 405,697

[22] Filed: Mar. 17, 1995

[51] Int. Cl.$^6$ .................................................. A61B 19/00
[52] U.S. Cl. .............................................. 128/897; 128/899
[58] Field of Search ...................... 128/897–99; 600/101, 600/117, 160, 178

[56] References Cited

U.S. PATENT DOCUMENTS 5,284,128  2/1994  Hart ............................................. 128/4

Primary Examiner—John P. Lacyk
Attorney, Agent, or Firm—Richard L. Myers

[57] ABSTRACT

A method for performing a surgical operation on a body conduit includes the step of inserting into the conduit an apparatus having at its distal end an element the location of which is detectable from regions exterior of the body. The apparatus is moved within the conduit until the element is positioned relative to a predetermined location where the element functions as a target. Detecting the location of this target within the conduit facilitates insertion of a surgical instrument percutaneously of the body and toward the predetermined location. The targeting apparatus may be used with an endoscope and may include a variety of active and passive elements which form the target. The surgical instrument can be inserted percutaneously transverse to the axis of the conduit to perform a variety of surgical operations. Sidebranch occlusion in an insitu procedure is greatly facilitated by this method and apparatus.

26 Claims, 3 Drawing Sheets

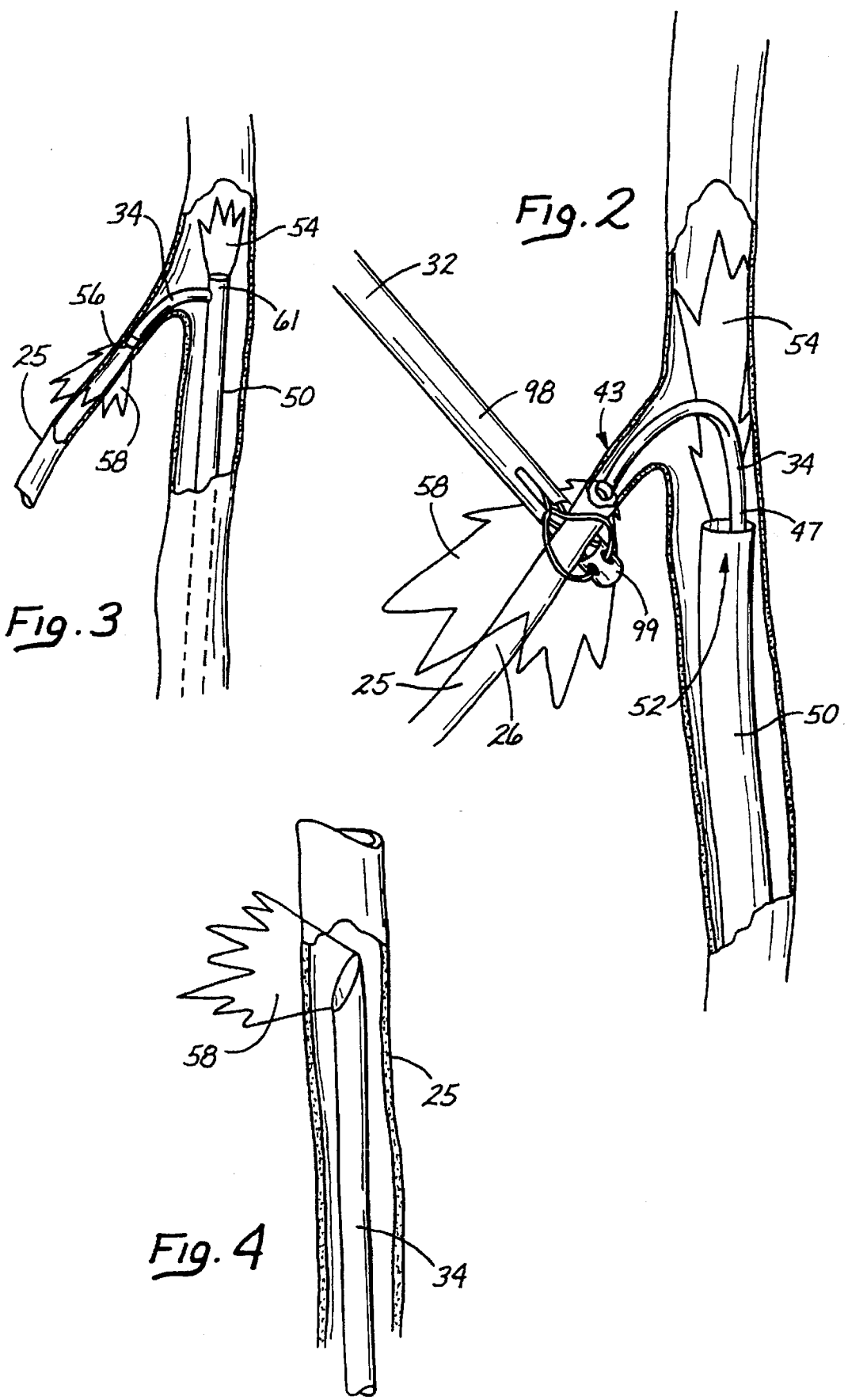

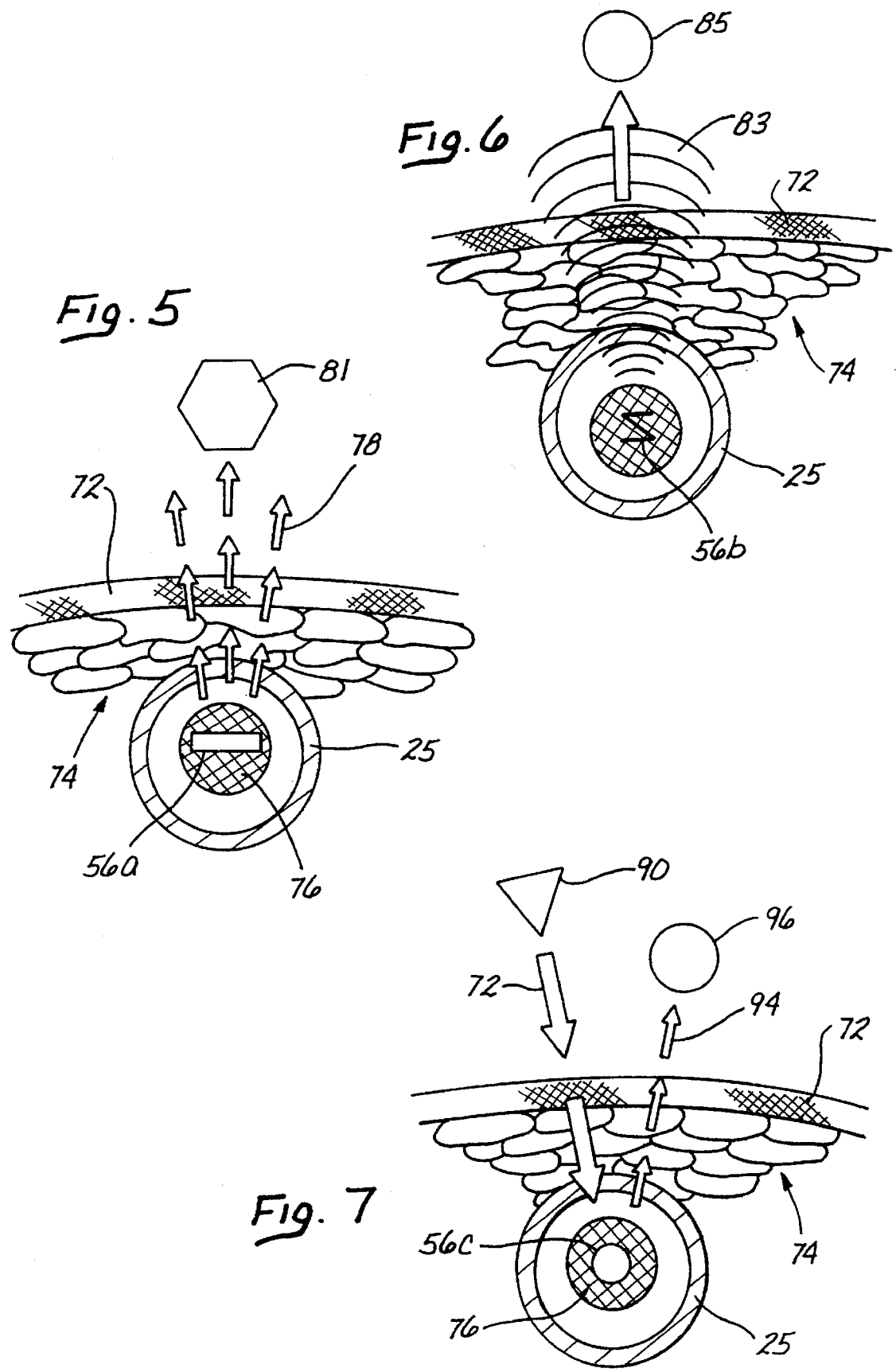

METHOD AND APPARATUS FOR ENDOCONDUIT TARGETING

BACKGROUND OF THE INVENTION

1. Field of the Invention

This invention relates generally to apparatus and methods for performing surgical functions percutaneously on body conduits.

2. Discussion of the Prior Art

As the age of a human body increases, the capacity of its vascular system to carry blood away from and back to the heart tends to degrade. This is caused in part by a hardening of the arteries or by deposits within the arteries which tend to gradually restrict arterial blood flow. When sufficient blood cannot reach an area of the body, the tissue in that area is not supplied with the nutrients and oxygen to sustain and regenerate itself.

Particularly in the aging population, this problem with circulation is particularly noticeable at the extremities, such as the lower leg and foot which are distantly removed from the heart. To supply these extremities with oxygen and nutrients, the blood travels from the heart through an arterial system to the distant location. The venous system gathers the blood at the extremity and returns it through veins back to the heart.

While gravity assists the function of the arteries, it inhibits the function of the veins which must return the blood upwardly through the leg and back to the heart. Assisting each vein in overcoming the gravitational force is a series of vein valves which permit the flow of blood upwardly in the vein, but inhibit the flow of blood downwardly through the vein.

In the past, degradation of the arterial system has been addressed by reconnecting the large saphenous vein in the leg so that it can function as an artery. This provides an additional conduit for transporting blood to the extremities. Although this procedure reduces the capacity of the venous system, it has been found that the remaining veins have been able to accommodate the increased blood flow.

Early procedures required that the saphenous vein be harvested or removed from the leg, turned end-for-end, and reconnected to the arterial system. This turning of vein was required in order to reorient the valves of the vein in a downward direction to facilitate arterial blood flow toward the extremity.

More recently, an insitu procedure has left the saphenous vein in place and the individual valves within the vein have been disrupted. When a valve is disrupted, it no longer functions to inhibit downward flow so that the vein can function as an artery.

As part of this insitu procedure, it is important to occlude the secondary veins which are attached to the saphenous vein. Failure to provide for this occlusion would drive the arterial blood backwardly into the venous system. It is the occlusion of these secondary vessels which is of particular interest to the present invention.

In the past, dye has been injected into the saphenous vein and, using fluoroscopy, the secondary vessels have been identified. In order to occlude these secondary vessels, various mechanisms have been proposed for insertion into the secondary vessel to clog the vessel and stop blood flow. This procedure has not been widely accepted. For one reason, the placement of objects within the vascular system is to be avoided whenever possible. Should the object become dislodged, it could easily migrate to inhibit blood flow in more important regions of the body.

Alternatively, a large incision has been made in the leg in order to gain direct access to the secondary vessel. With this direct access, a suture or clamp has been applied for occlusion. Of course, a large incision is always to be avoided if a less invasive technique can accomplish the same objective.

In either case, the targeting of a secondary vessel has been difficult. As noted, fluoroscopy has been used. However, this passive technique for targeting a secondary vessel is cumbersome, expensive and not particularly accurate.

SUMMARY OF THE INVENTION

In accordance with the present invention, these deficiencies of the prior art are overcome with an apparatus and method which provides for the insertion of an element through the primary conduit and into the secondary conduit. The presence of this element at a predetermined location is detectable from regions exterior of the body where it can be used as a target for instruments inserted percutaneously, directed toward the target.

In a particular embodiment the element may be active as in the case of a light fiber which is inserted with or without an endoscope into the saphenous vein. Visualization through the endoscope enables one to see a sidebranch which needs to be occluded. Then the light fiber can be guided into the sidebranch, for example by deflecting the fiber off of the body of the endoscope, and into the sidebranch. In this location, the light at the tip of the fiber forms a point target which is directly visible from regions exterior of the body. Inserting an instrument percutaneously and guiding the instrument toward the point target enables the surgeon to occlude the sidebranch. The particular instrument which accomplishes the occlusion may be a ligator, clip applier, laser, or cautery device, for example.

Where the element forming the target is an optical fiber, the target light can be provided with characteristics which distinguish it from the light of the endoscope. In one embodiment, the light of the target element is transmitted through a green filter in order to accentuate the target in an otherwise generally red environment.

Other active target elements can be inserted through the primary conduit and into the secondary conduit. For example, a permanent magnet or electromagnet can be inserted where its location is detected from the exterior of the body by a magnetic detector. Alternatively, the active element may include a heater which is detectable by way of an IR detector from regions exterior of the body. A sonic transmitter in the form of ultrasound, piezoelectric crystal, or wire can be used as the active element to form a target detectable from regions exterior of the body. An inactive element can also be positioned at the predetermined location. Such an element can be used as a reflector so that its location can be determined. In one instance, resonant energy is transmitted from outside the body to a transducer or piezoelectric device which forms the target element. The energy emanating from this element can then be detected to determine the position of the target.

This system is particularly appreciated by those who object to the insertion of occluding objects interiorly of the body conduits. Since the occluding device can be inserted percutaneously, a large incision is not required in order to gain access to the conduit. The resulting simplicity of the concept reduces the time, cost and trauma associated with the procedure.

In one aspect of the invention, a method for performing a surgical operation on a conduit within a human body comprises the steps of inserting into the body conduit an elongate apparatus having a first axis. The apparatus has an element disposed at its distal end which is adapted to provide an indication of the location of the device within the conduit. The device can then be moved axially through the conduit until the element is located relative to a predetermined position along the conduit. Activating the element within the conduit produces a target which is positioned relative to the predetermined location where it can be detected from a location exterior of the body to determine the predetermined location. Then a surgical instrument with a sharp distal tip can be percutaneously inserted into the body. Guiding this instrument along its axis toward the target enables the surgical instrument to be operated at the predetermined location to perform the surgical operation.

In another aspect of the invention, a method is disclosed for performing a surgical procedure on one of a series of body conduits. These conduits include a primary conduit and a secondary conduit extending laterally from the primary conduit. The method includes the step of inserting into the primary conduit an apparatus having a first energy source and portions defining a lumen. Issuing from the lumen a second energy source enables one to guide the second source laterally into the secondary conduit where it can be positioned to form a target relative to a predetermined location. A surgical instrument can then be inserted percutaneously into the body and guided toward the target from regions exterior of the body. At the predetermined location the surgical instrument can be operated to perform the surgical operation on the secondary conduit.

A further aspect of the invention includes a surgical apparatus for illuminating a series of body conduits including a primary conduit and a secondary conduit. The apparatus includes an elongate tube having a proximal end, a distal end and portions defining a lumen. A first light source provides a first light emanating from the distal end of the tube and having first characteristics. A second light source, movable along the lumen of the tube to regions exterior of the tube, the second light source provides a second light having second characteristics different from the first energy characteristics of the first light. The surgical apparatus also includes means for directing the second light laterally of the tube and into the secondary conduit.

These and other features and advantages of the invention will become more apparent with a discussion of preferred embodiments and method steps, and reference to the associated drawings.

DESCRIPTION OF THE DRAWINGS

FIG. 2 is an enlarged perspective view of the junction between the saphenous vein and one of the sidebranches showing an endoscope with a first light source and an optical fiber providing a second light source;

FIG. 3 is a top plan view similar to FIG. 2 and illustrating an embodiment of the endoscope which includes a deflector for guiding the optical fiber laterally into the sidebranch;

FIG. 4 is a side view of a light fiber beveled at its tip to provide a target in the form of directable light;

FIG. 5 is a radial cross section view of a body conduit and an active target element generating heat or magnetic waves detectable outside the body;

FIG. 6 is a radial cross section view similar to FIG. 5 and illustrating an active target element generating ultrasonic or sonic RF waves detectable from outside the body; and FIG. 7 is a radial cross section view similar to FIG. 5 and illustrating a passive target element receiving transmitted waves from regions outside the body, and reflecting those waves to form a target detectable from regions outside the body.

DESCRIPTION OF PREFERRED EMBODIMENT AND BEST MODE OF THE INVENTION

Figure 1:
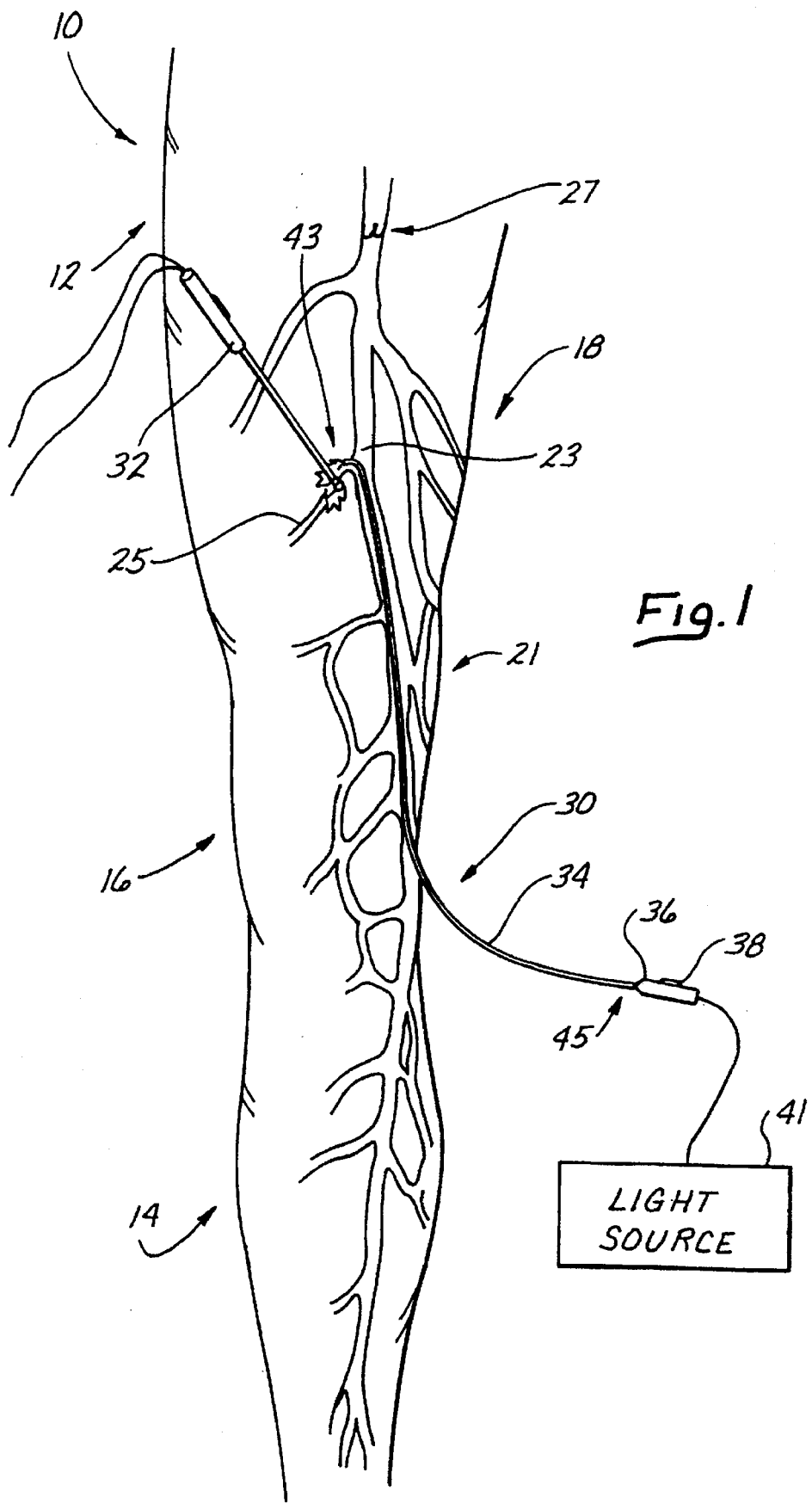
FIG. 1 is a perspective view of a human leg illustrating the saphenous vein and various sidebranches associated therewith.

A human leg is illustrated in FIG. 1 and designated generally by the reference numeral 10. The leg 10 includes an upper leg or thigh 12, a lower leg or shin 14, and a knee 16 disposed therebetween. A vascular system 18 is disposed within the leg 10 and provides a series of conduits for transporting blood from the heart (not shown) to the extremities such as the lower leg 14.

Although the vascular system 18 includes an arterial system for transporting blood to the lower leg 14, and a venous system 21 for carrying blood away from the lower leg 14, only the venous system 21 is illustrated for clarity. This venous system 21 includes a series of conduits in the form of vessels. A primary conduit, such as the saphenous vein, is designated by the reference numeral 23, while a secondary conduit, forming a tributary or sidebranch of the primary conduit 23, is designated by the reference numeral 25. The sidebranch 25 is shown with an axis 26 which extends along its length.

In order to facilitate the function of the venous system 21 in carrying blood against the force of gravity upwardly in the leg 10, the saphenous vein 23 includes a series of valves, such as the valve 27 which is illustrated in its natural state. Each of these valves 27 is configured and oriented within the vein 23 to permit blood flow upwardly in the vein 23 but to inhibit blood flow downwardly in the vein 23.

In a surgical procedure for increasing the circulation of blood to the lower leg 14, the saphenous vein 23, which typically carries blood away from the lower leg 14, is transformed into an artery for carrying blood to the lower leg 14. In a preferred "insitu" procedure, the valves 27 in the saphenous vein 23 are disrupted. This disruption of the valve 27 permits the flow of blood in the reverse direction downwardly in the leg 10, so that the primary conduit 23 can now be used to carry blood toward the lower leg 14.

As part of this insitu procedure, it is desirable to occlude the tributaries or secondary conduits, such as the sidebranch 25. In the past, this has been accomplished by introducing occlusion devices into the sidebranch 25 where they are adapted to frictionally engage the sidewalls of the sidebranch 25 in order to occlude the vessel. Unfortunately, if the occluding device becomes dislodged, it is free to pass through the secondary conduit 25 into the primary conduit 23 where it can cause severe complications and even death for the patient.

One of the purposes of the present invention is to occlude the sidebranch 25 by inserting a surgical instrument percutaneously through the leg 10 where the sidebranch 25 can be engaged from the outside and ligated or clamped to provide occlusion. In a preferred method of the invention, this is accomplished by inserting the surgical instrument percutaneously with or without a pre-incision. The procedure is further facilitated by positioning within the sidebranch 25 a targeting device the location of which is detectable from regions outside the leg 10. In FIG. 1 the targeting device is designated by the reference numeral 30, while the surgical device is designated by the reference numeral 32.

Although the vascular system 18 is illustrated and discussed as exemplary of the method and apparatus of this invention, it will be apparent that there are many other body conduits which can benefit from this concept which provides for a target within the conduit and a surgical device percutaneously insertable to perform a surgical function on that conduit.

In a preferred embodiment, the targeting device 30 includes an optical fiber 34 and a handle 36 having a finger tab 38. The fiber 34 is connected through the handle 36 to a light source 41. In this embodiment, the optical fiber 34 extends from a distal end 43 to a proximal end 45 and has an axis 47 best illustrated in the detail of FIG. 2.

In the embodiment of FIG. 1, the targeting device 30 can be of the type disclosed and claimed by applicant in U.S. Pat. No. 5,284,128, issued Feb. 8, 1994. This device has at its distal end 43 a series of notches which enable the optical fiber 34 to be deflected by operation of the finger tab 38. These characteristics permit the optical fiber 34 to be inserted into the saphenous vein 23 and deflected laterally into the sidebranch 25. In this location the light from the source 41, which emanates from the distal end 43 of the fiber 34, provides a target in the sidebranch 25. In the case of a light fiber 34, the target is active rather than passive and provides a location visible from outside the leg 10 to aid in guiding the surgical instrument 32 toward a predetermined location within the sidebranch 25.

In the embodiment of FIG. 2, the light fiber 34 is used in combination with an angioscope 50 having a plurality of lumens 52. These lumens 52 are dedicated to a primary light source, represented by the light pattern 54, and a secondary light source in the form of the light fiber 34. The lumens 52 will also typically include a working channel of the angioscope 50. At its distal end 43, the light fiber 34 provides a targeting element 56 in the form of a fiber tip which radiates light in a secondary light pattern 58.

In a preferred method of operation, the angioscope 50 is inserted into the saphenous vein 23 through an incision in the vicinity of the knee 16. The primary light source, associated with the light pattern 54 of the angioscope 50, is activated as the angioscope 50 is inserted upwardly through the saphenous vein 23. This light pattern 54 and the optics associated with the angioscope 50 enable the surgeon to locate the various sidebranches, such as the sidebranch 25.

With the angioscope 50 suitably positioned, the light fiber 34 can be issued from the angioscope 50 and manipulated into the sidebranch 25. Once the targeting element 56, such as the distal tip of the fiber 34 is suitably positioned relative to the predetermined location, the secondary light source, associated with the light pattern 58, can be activated to form an intravascular target.

In a preferred apparatus, the primary light source associated with the pattern 54 and the secondary light source associated with the pattern 58, have different energy characteristics. For example, the first light source can provide a white light which aids in locating the sidebranch 25. In order to distinguish the secondary pattern 58 from the primary pattern 54, the secondary light source can be provided with a different color. In the best mode of the invention, this light is filtered to provide a green color which offers considerable contrast to the white light of the pattern 54 and the red color normally associated with a tissue environment. In order to further accentuate the targeting element 56, the primary light source can be extinguished so that only the second light pattern is visible from regions outside the body.

FIG. 3 illustrates a further embodiment of the invention wherein the optical fiber 34 is not self-deflecting. In this embodiment, the angioscope 50 is provided with a deflection member 61 which receives the fiber moving axially through the angioscope 50 and deflects the fiber 34 laterally into the sidebranch 25.

In some cases it may be desirable if the targeting element 56 is characterized so that its light energy projects only in a single direction. This enables the second light pattern 58 to be illustrated only from a given side of the fiber 34. The fiber 34 can then be turned on its axis until the brightest optical effect is achieved. This tends to increase the point source of the targeting element 56. In a preferred embodiment, the fiber 34 is provided with a bevel 63 at its distal end 43 so that the light pattern 58 radiates in the single direction.

It will be apparent that there are many forms of energy that can function as a target other than the visible light energy associated with the optical fiber 34. The source of energy can be either active or passive, although the active sources are preferred for most applications.

Referring now to FIGS. 5-7, the sidebranch 25 is illustrated in radial cross section along with a layer of skin 72 and a thickness of fat cells 74. In FIG. 5 the targeting element, which is typically mounted at the distal end of a catheter or guidewire 76 includes a permanent magnet or electromagnet designated by the reference numeral 56a. Alternatively, the targeting element 56a can be a heat source. In either event, energy waves emanate from the target 56a as illustrated by arrows 78, to regions exterior of the body.

In this exterior region, a detector 81 can be provided to determine the direction and distance from the targeting element 56a. If this element 56a is a heat source, the detector 81 will typically be an infrared detector. Alternatively, if the targeting element 56a is a magnet, the detector 81 will typically be a magnetic detector.

In FIG. 6, the targeting element comprises an ultrasonic, sonic or radio frequency transmitter or emitter. A piezoelectric crystal, representative of this type of targeting element, is designated by the reference numeral 56b. Energy waves emanating from this targeting element 56b are in the form of electrical waves 83, and are detectable exteriorly of the body by an ultrasonic or RF detector 85.

It will be noted that both of the targeting elements 56a and 56b in FIGS. 5 and 6 are active elements in that they generate energy which passes through the skin 72 and is detectable outside the body. In contrast, a passive element is illustrated in FIG. 7. In this case, the targeting element, designated by the reference numeral 76c, is a transducer or piezoelectric crystal. A transmitter 90 positioned outside the body can be used to direct energy toward the targeting element 56c in the form of the large arrows 92. This energy is reflected or otherwise transmitted back from the targeting element 56c in the form of the smaller arrows 94. A detector 96 appropriately positioned to receive the reflected energy represented by the arrow 94 is then used to locate the target.

Regardless of the type of element used as a target the surgical instrument 32 can be inserted percutaneously through the skin 72 and toward the predetermined location. This location may not be exactly at the targeting element 56, but will more likely be slightly ahead of that element 56 where the sidebranch 25 is not occupied. At this location, many different surgical instruments can be used to perform a predetermined surgical function on the conduit. The instrument 32 will typically have an axis 98 extending to a distal tip 99.

In the case of the sidebranch 25 and the insitu procedure, the surgical device 32 will typically be adapted to occlude the vessel from regions outside the vessel. The surgical instrument 32 particularly preferred for this purpose is a ligating device which can be used to tie a suture around the sidebranch 25. A device of this type is illustrated in FIG. 2. Alternatively, the instrument 32 may be a clip applier which will position a clip around the sidebranch 25 to accomplish the occlusion. Lasers can also be used for this purpose. YAG lasers, ARGON lasers and KIP lasers are all well-known to form blood clots, which can be relied on to occlude the vessel 25. Electrosurgical apparatus, or a D.C. cauterizing electrode or other point heat source, could also be used to occlude the sidebranch 25. Each of these surgical instruments is represented by the instrument designated by the reference numeral 32 in FIG. 2.

Although the invention has been described with reference to particular types of targeting elements and surgical instruments, it will be apparent that the concept is broader than these specific combinations. The mere provision of a target, typically using an active element within a body conduit, and the use of that target to guide an instrument percutaneously toward the conduit, can apply to any body conduit and any surgical function associated with the instrument. The specific targeting element can be any element providing an indication of its location within the conduit. While this will typically be a point source of energy, it is clear that the energy can be either generated by the element, as is the case of an active element, or reflected by the element, as is the case with a passive element. It is the detection from outside the body of the specific location of the targeting element which enables the surgeon to guide the instrument to the predetermined location along the conduit.

Given the wide variations within this concept, one is cautioned not to restrict the invention to the embodiments which have been specifically disclosed and illustrated, but rather encouraged to determine the scope of the invention only with reference to the following claims.

We claim:

1. A method for performing a surgical operation on a conduit within a human body, comprising the steps of:
    inserting into the body conduit an elongate apparatus having a first axis extending between a distal end and a proximal end, the apparatus having at its distal end an element adapted to provide an indication of the location of the distal end of the device within the conduit;
    moving the apparatus axially through the conduit until the element is positioned relative to a predetermined location along the conduit;
    activating the element to produce a target positioned relative to the predetermined location along the conduit;
    detecting the activated element from a location exterior of the body to ascertain the predetermined location along the conduit;
    inserting percutaneously into the body a surgical instrument having a second axis extending to a distal tip;
    guiding the instrument along the second axis and toward the target; and
    operating the surgical instrument to perform the surgical operation on the conduit at the predetermined location.

2. The method recited in claim 1 wherein the second inserting step includes the step of inserting the surgical instrument along the second axis and transverse to the first axis of the conduit.

3. The method recited in claim 1 wherein the first inserting step includes the step of inserting into the conduit the device in the form of an active element adapted to emit waves radiating from the element to regions exterior of the body.

4. The method recited in claim 3 wherein the waves radiating from the element are light waves.

5. The method recited in claim 4 wherein the light waves are in the visible spectrum and the activating step includes the step of illuminating the element to form a visible target relative to the predetermined location.

6. The method recited in claim 3 wherein the waves are electrical waves.

7. The method recited in claim 3 wherein the waves are magnetic waves.

8. The method recited in claim 3 wherein the waves are heat waves.

9. The method recited in claim 3 wherein the second inserting step includes the step of inserting into the body an occluding device and the operating step includes the step of operating the device to occlude the conduit at the predetermined location.

10. The method recited in claim 9 wherein the occluding device is a ligating device.

11. A method for performing a surgical procedure on one of a series of body conduits including a primary conduit and a secondary conduit extending laterally from the primary conduit, comprising the steps of:
    inserting into the primary conduit an apparatus having a first energy source and portions defining a lumen;
    issuing from the lumen a second energy source;
    guiding the second energy source laterally into the secondary conduit to form a target positioned relative to a predetermined location along the secondary conduit;
    inserting percutaneously into the body a surgical instrument adapted to perform the surgical procedure;
    guiding the surgical instrument toward the target from regions exterior of the body; and
    operating the surgical instrument to perform the surgical operation on the secondary conduit at the predetermined location.

12. The method recited in claim 11 wherein the first inserting step includes the step of inserting into the primary conduit the first energy source in the form of a primary light source providing light at a first frequency.

13. The method recited in claim 12 wherein the issuing step includes the step of issuing from the lumen of the first energy source, the secondary energy source in the form of a secondary light source providing light at a second frequency.

14. The method recited in claim 12 wherein the second frequency of the second light source is different than the first frequency of the first light source.

15. The method recited in claim 14 further comprising the step of:
    detecting the second frequency of the second light source from regions exterior of the body.

16. The method recited in claim 13 further comprising the steps of:
    activating the first light source to locate the secondary conduit; and
    activating the second light source to form the target along the secondary conduit.

17. The method recited in claim 16 further comprising the step of:
    deactivating the first light source while the target is being formed by the second light source.

18. The method recited in claim 16 further comprising the step of:
    filtering the secondary light source in order to enhance the contrast of the target.

19. The method recited in claim 18 further comprising the step of:

filtering the secondary light source in order to enhance the visual contrast of the target relative to the secondary conduit.

20. A surgical apparatus for illuminating a series of body conduits including a primary conduit and a secondary conduit extending laterally from the primary conduit, the apparatus comprising:

an elongate tube adapted for insertion into the primary body conduit and having a proximal end, a distal end, and portions of the tube defining a lumen;

a first energy source providing energy emanating from the distal end of the tube and having first energy characteristics;

a second energy source movable along the tureen of the tube to regions exterior of the tube, the second energy source providing energy with second energy characteristics different than the first energy characteristics of the first energy source; and the second energy source being adapted for movement laterally of the tube and into the secondary conduit.

21. The apparatus recited in claim 20 wherein the first energy source provides light energy having the first characteristics in the form of a first frequency.

22. The apparatus recited in claim 21 wherein the second energy source includes an optical fiber movable axially along the lumen of the tube.

23. The apparatus recited in claim 22 wherein the optical fiber has an axis and the second light emanates from the optical fiber in a predetermined direction laterally of the axis of the fiber.

24. The apparatus recited in claim 20 wherein the second energy source provides energy in the form of magnetic waves.

25. The apparatus recited in claim 20 wherein the second energy source provides energy in the form of electrical waves.

26. The apparatus recited in claim 20 wherein the second energy source provides energy in the form of heat waves.

* * * * *